United States Patent
Silver et al.

(10) Patent No.: US 10,417,795 B2
(45) Date of Patent: Sep. 17, 2019

(54) ITERATIVE RECONSTRUCTION WITH SYSTEM OPTICS MODELING USING FILTERS

(71) Applicant: CANON MEDICAL SYSTEMS CORPORATION, Otawara-shi (JP)

(72) Inventors: Michael D. Silver, Northbrook, IL (US); Ilmar A. Hein, Chicago, IL (US); Alexander A. Zamyatin, Hawthorn Woods, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/681,797

(22) Filed: Apr. 8, 2015

(65) Prior Publication Data

US 2016/0300369 A1  Oct. 13, 2016

(51) Int. Cl.
| | |
|---|---|
| *A61B 6/00* | (2006.01) |
| *A61B 6/03* | (2006.01) |
| *G06T 5/20* | (2006.01) |
| *G06T 11/00* | (2006.01) |

(52) U.S. Cl.
CPC ............ *G06T 11/006* (2013.01); *A61B 6/032* (2013.01); *G06T 5/20* (2013.01); *A61B 6/5229* (2013.01); *G06T 2207/10081* (2013.01); *G06T 2211/421* (2013.01); *G06T 2211/424* (2013.01)

(58) Field of Classification Search
CPC ...................... G06T 5/20; G06T 11/006; G06T 2207/10081; G06T 2211/421; G06T 2211/424; A61B 6/032; A61B 6/5229
See application file for complete search history.

(56) References Cited

U.S. PATENT DOCUMENTS

| | | | | |
|---|---|---|---|---|
| 6,266,388 B1* | 7/2001 | Hsieh | ..................... | A61B 6/032 378/15 |
| 8,233,586 B1* | 7/2012 | Boas | ....................... | G06T 5/002 378/207 |
| 9,524,567 B1* | 12/2016 | Brokish | ................ | G06T 11/006 |
| 9,836,872 B2* | 12/2017 | Erhard | .................... | G06T 15/08 |
| 2005/0058240 A1* | 3/2005 | Claus | .................... | G06T 11/006 378/22 |
| 2005/0286749 A1* | 12/2005 | De Man | ................ | G06T 11/005 382/131 |

(Continued)

OTHER PUBLICATIONS

Capel, David "Super-resolution: Maximum Likelihood and Related Approaches", Chapter 5 of "Image Mosaicing and Super-Resolution", 2004, 81-136.*
Zamyatin et al., "Practical Hybrid Convolution Algorithm for Helical CT Reconstruction", 2006, IEEE Transactions on Nuclear Science, vol. 53, No. 1, 167-174.*

(Continued)

*Primary Examiner* — Katrina R Fujita
(74) *Attorney, Agent, or Firm* — Oblon, McClelland, Maier & Neustadt, L.L.P.

(57) ABSTRACT

A CT imaging apparatus has processing circuitry that is configured to obtain projection data collected by a CT detector during a scan of an object. The processing circuitry is also configured to perform iterative reconstruction of the projection data to generate a current image. The iterative reconstruction includes filtering forward-projected data during backprojection or filtering image data prior to forward projection to model system optics. The processing circuitry is also configured to combine the current image with a previously-obtained image to generate an updated image.

20 Claims, 20 Drawing Sheets

(56) References Cited

U.S. PATENT DOCUMENTS

| | | | | |
|---|---|---|---|---|
| 2006/0257010 A1* | 11/2006 | George | G06T 11/006 | 382/131 |
| 2007/0280404 A1* | 12/2007 | Nielsen | G06T 11/006 | 378/4 |
| 2008/0240335 A1* | 10/2008 | Manjeshwar | A61B 6/032 | 378/4 |
| 2009/0016485 A1* | 1/2009 | Nakanishi | G06T 11/008 | 378/19 |
| 2009/0060121 A1* | 3/2009 | Ziegler | A61B 6/032 | 378/8 |
| 2010/0183203 A1* | 7/2010 | Ye | G01T 1/164 | 382/128 |
| 2012/0086850 A1* | 4/2012 | Irani | G06T 3/4053 | 348/441 |
| 2012/0155728 A1* | 6/2012 | DeMan | G06T 11/006 | 382/131 |
| 2013/0177225 A1* | 7/2013 | Zamyatin | G06T 11/006 | 382/131 |
| 2013/0294665 A1* | 11/2013 | Rao | G01S 15/8977 | 382/131 |
| 2014/0212018 A1* | 7/2014 | Hein | G06T 11/008 | 382/132 |
| 2014/0369581 A1* | 12/2014 | Fu | G06T 11/006 | 382/131 |
| 2015/0036902 A1* | 2/2015 | Zamyatin | G06T 7/0012 | 382/131 |

OTHER PUBLICATIONS

Hein et al. "System optics in both backprojection and forward projection for model-based iterative reconstruction." Medical Imaging 2012: Physics of Medical Imaging. vol. 8313. International Society for Optics and Photonics, 2012.*

Fu et al. "Modeling and estimation of detector response and focal spot profile for high-resolution iterative CT reconstruction." 2013 IEEE Nuclear Science Symposium and Medical Imaging Conference (2013 NSS/MIC). IEEE, 2013. (Year: 2013).*

Katsura et al. "Model-based iterative reconstruction technique for radiation dose reduction in chest CT: comparison with the adaptive statistical iterative reconstruction technique." European radiology 22.8 (2012): 1613-1623. (Year: 2012).*

Prakash et al. "Radiation dose reduction with chest computed tomography using adaptive statistical iterative reconstruction technique: initial experience." Journal of computer assisted tomography 34.1 (2010): 40-45. (Year: 2010).*

Seibert, James Anthony. "Iterative reconstruction: how it works, how to apply it." Pediatric radiology 44.3 (2014): 431-439. (Year: 2014).*

Yu et al. "Fast model-based X-ray CT reconstruction using spatially nonhomogeneous ICD optimization." IEEE Transactions on image processing 20.1 (2011): 161-175. (Year: 2011).*

Jean-Baptiste Thibault, et al., "A three-dimensional statistical approach to improved image quality for multislice helical CT", Medical Physics, vol. 34 No. 11, Nov. 2007, pp. 4526-4544.

* cited by examiner $DLPP\ x_v, y_v, \beta\ [i]$ = $DTH\ x_v, y_v, \beta\ [i]$ ⊗ $DGS\ x_v, y_v, \beta\ [i]$ $NPIS_{DLPP}\ x_v, y_v, \beta$    $NPIS_{TH}\ x_v, y_v, \beta$    $NPIS_{GS}\ x_v, y_v, \beta$

Obtaining projection data, via a processing circuit, collected by a CT detector during a scan of an object
S1810

Performing iterative reconstruction (IR) of the projection data by filtering forward projected data during backprojection to model system optics
S1820

Subtracting the filtered forward projected data from the projection data to generate a current image
S1830

Combining the current image with a previously-obtained image to generate an updated image
S1840

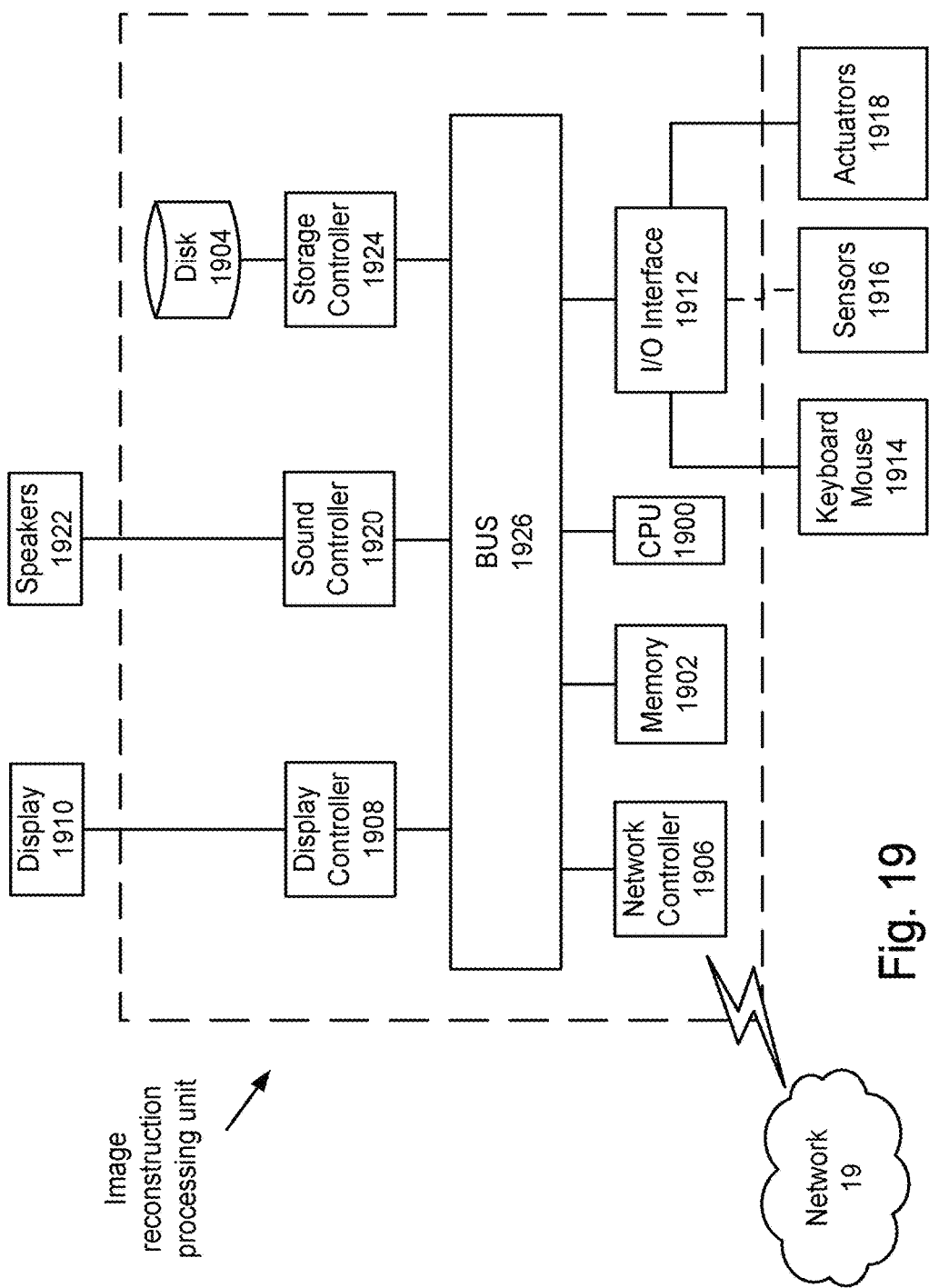

ITERATIVE RECONSTRUCTION WITH SYSTEM OPTICS MODELING USING FILTERS

FIELD

Embodiments disclosed herein generally relate to iterative reconstruction in computed tomography (CT) imaging using system optics modeling.

BACKGROUND

The X-ray beam in most computed tomography (CT) scanners is generally polychromatic. Yet, third-generation CT scanners generate images based upon data according to the energy integration nature of the detectors. These conventional detectors are called energy-integrating detectors and acquire energy integration X-ray data. On the other hand, photon-counting detectors are configured to acquire the spectral nature of the X-ray source, rather than the energy integration nature. To obtain the spectral nature of the transmitted X-ray data, the photon-counting detectors split the X-ray beam into its component energies or spectrum bins and count the number of photons in each of the bins. The use of the spectral nature of the X-ray source in CT is often referred to as spectral CT. Since spectral CT involves the detection of transmitted X-rays at two or more energy levels, spectral CT generally includes dual-energy CT by definition.

Spectral CT is advantageous over conventional CT because spectral CT offers the additional clinical information included in the full spectrum of an X-ray beam. For example, spectral CT facilitates in discriminating tissues, differentiating between tissues containing calcium and tissues containing iodine, and enhancing the detection of smaller vessels. Among other advantages, spectral CT reduces beam-hardening artifacts, and increases accuracy in CT numbers independent of the type of scanner.

Conventional attempts include the use of integrating detectors in implementing spectral CT. One attempt includes dual sources and dual integrating detectors that are placed on the gantry at a predetermined angle with respect to each other for acquiring data as the gantry rotates around a patient. Another attempt includes the combination of a single source that performs kV-switching and a single integrating detector, which is placed on the gantry for acquiring data as the gantry rotates around a patient. Yet another attempt includes a single source and dual integrating detectors that are layered on the gantry for acquiring the data as the gantry rotates around a patient. All of these attempts at spectral CT were not successful in substantially solving issues, such as beam hardening, temporal resolution, noise, poor detector response, poor energy separation, etc., for reconstructing clinically viable images.

Iterative reconstruction (IR) can be incorporated into a CT scanner system, such as one of the CT scanners described above. IR compares a forward projection, through an image estimate, to the measured data. Differences are used to update the image estimate. Measured data includes the true system optics, which blurs the data, as well as physical effects, such as scatter and beam hardening. When the reprojected data and measured data match, a good estimate of the true solution is obtained as a reconstructed image. Conventionally, reconstruction assumed a point source, a point detector, point image voxels, and snapshot acquisition, which is called pencil beam geometry.

For low-dose applications, data fidelity implies also matching the noise, which is not desirable. Therefore, most systems use a "cost function" inserted into the iterations in order to reduce noise while maintaining true features.

System optics modeling (SOM) includes knowing (1) the extent of the source and how its emissivity varies with position, (2) the size of the detector element, (3) the relative geometry (system magnification) of the source and detector elements, (4) image voxel size and shape, and (5) the rotation of the gantry during each data sample.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 7 illustrates a final DLPF filter according to one embodiment;

FIG. 18 is a flowchart for a method of reconstructing a detected X-ray from an X-ray source of a CT scanner according to one embodiment; and FIG. 19 is a block diagram of a computing system used according to embodiments described herein.

DETAILED DESCRIPTION

Embodiments described herein are directed to an iterative reconstruction with system optics modeling using filters. In one embodiment, a CT imaging apparatus has processing circuitry that is configured to obtain projection data collected by a CT detector during a scan of an object. The processing circuitry is also configured to perform iterative reconstruction of the projection data to generate a current image. The iterative reconstruction includes filtering forward-projected data during backprojection to model system optics. The processing circuitry is also configured to combine the current image with a previously-obtained image to generate an updated image.

In one embodiment, a method of performing image reconstruction includes obtaining projection data collected by a CT detector during a scan of an object. The method also includes performing iterative reconstruction of the projection data to generate a current image. The performing step includes filtering forward-projected data during backprojection to model system optics. The method also includes combining the current image with a previously-obtained image to generate an updated image. In another embodiment, a computer-readable medium has computer-executable instructions embodied thereon, that when executed by a computing device, causes the computing device to perform the above-described method.

Figure 1:
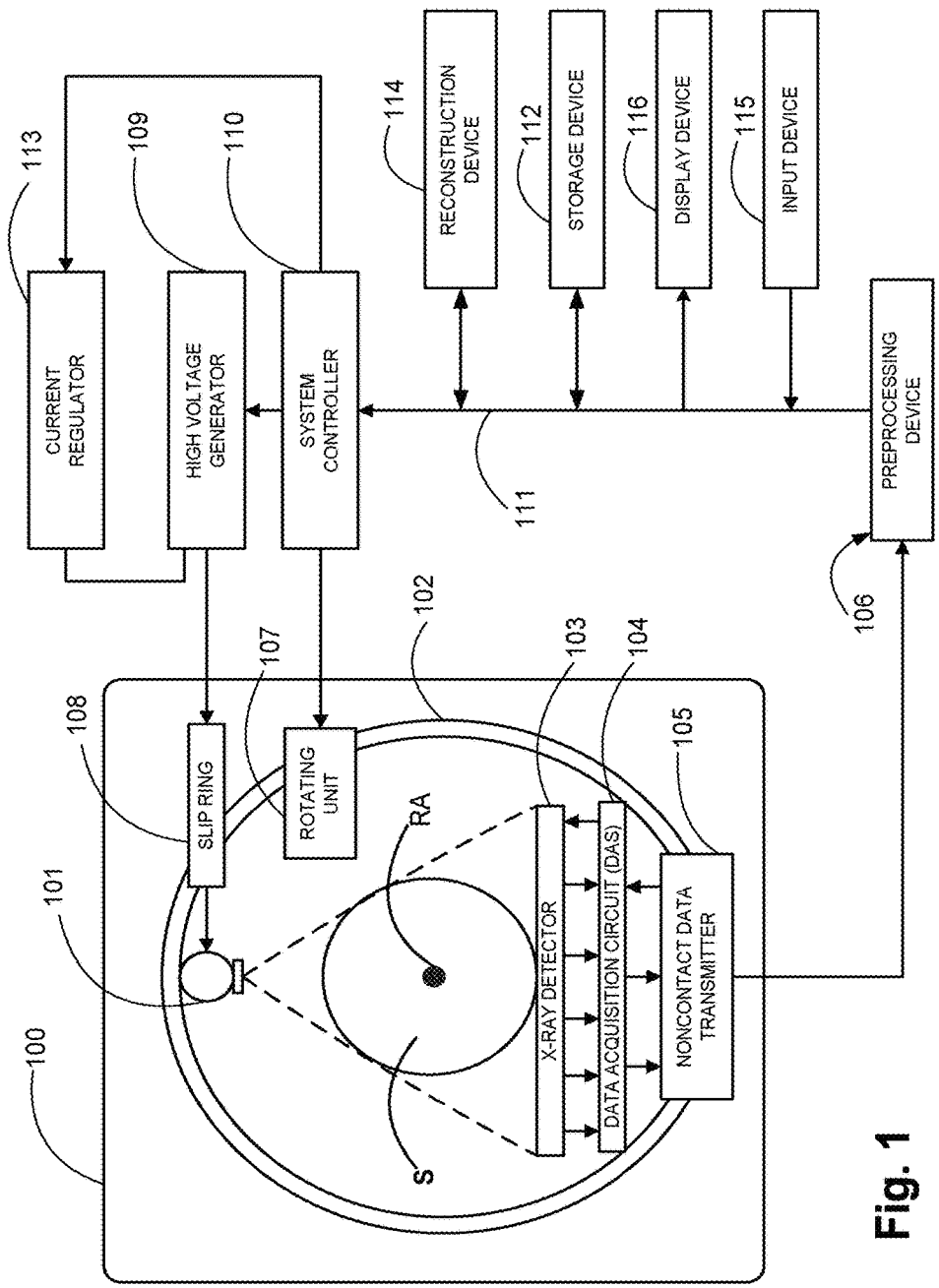
FIG. 1 illustrates an implementation of a CT system according to one embodiment.

FIG. 1 illustrates an implementation of a CT apparatus or scanner. As shown in FIG. 1, the radiography gantry 100 is illustrated from a side view and further includes an X-ray tube 101, an annular frame 102, and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the annular frame 102 at a high speed, such as 0.4 sec/rotation, while the subject S is being moved along the axis RA into or out of the illustrated page.

The multi-slice X-ray CT apparatus further includes a high-voltage generator 109 that generates a tube voltage applied to the X-ray tube 101 through a slip ring 108 so that the X-ray tube 101 generates X-rays. The X-rays are emitted towards the subject S, whose cross sectional area is represented by a circle. The X-ray detector 103 is located at an opposite side from the X-ray tube 101 across the subject S for detecting the emitted X-rays that have been transmitted through the subject S. The X-ray detector 103 further includes individual detector elements or units.

With continued reference to FIG. 1, the CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A storage device 112 stores the resultant data, which is also called projection data at a stage immediately before reconstruction processing. The storage device 112 is connected to a system controller 110 through a data/control bus 111, together with a reconstruction device 114, input device 115, and display device 116.

The detectors are rotated and/or fixed with respect to the patient among various generations of the CT scanner systems. The above-described CT system is an example of a combined third-generation geometry and fourth-generation geometry system. In the third-generation system, the X-ray tube 101 and the X-ray detector 103 are diametrically mounted on the annular frame 102 and are rotated around the subject S as the annular frame 102 is rotated about the rotation axis RA. In the fourth-generation geometry system, the detectors are fixedly placed around the patient and an X-ray tube rotates around the patient.

In an alternative embodiment, the radiography gantry 100 has multiple detectors arranged on the annular frame 102, which is supported by a C-arm and a stand.

Conventional IR approaches have several exemplary problems when implemented with a CT scanner system, such as one or more of the CT scanner systems described above. In a first example, standard reconstruction by filtered backprojection requires adaptive filtering for low-dose acquisitions. However, such systems have difficulty maintaining resolution, especially within soft-tissue boundaries.

In a second example, since IR is often used for low-dose CT, cost functions are used, which can be based on total variation, anisotropic diffusion, bilateral filters, etc. However, all of these approaches have difficulty distinguishing between noise dots and small features, such as secondary and tertiary blood vessels in CTA scans. Another problem is the maintaining of the sharpness of boundaries of soft tissue organs. One conventional system solves this problem by incorporating the system optics model (SOM), which attempts to include the true beam width of the image system in the image reconstruction process. However, in such a system, the processing time is too large.

In a third example, the standard method for incorporating the SOM is to average multiple measurements around an isocenter. This provides the benefit of an image region near the isocenter and a reasonable approximation away from the isocenter. However, an example of an average taken over many micro-rays could include each detector sensor being broken into a 5×5 array of micro-sensors, the focal spot being broken into a 7×3 array of focal spots (each with its own emissivity function), and 5 micro-views being used to account for signal integration during rotation for each recorded view signal. IR already increases the computational load by an order of magnitude, and standard SOM increases the load an additional 5×5×7×3×5=2625 times. Further, if the number of microarrays is reduced, the benefits of using a SOM could be lost.

The disclosed embodiments described herein maintain and even improve image sharpness while using a cost function for noise reduction, without a substantial increase in computational complexity beyond IR without SOM. In one embodiment, the system optics are modeled as a spatially and view-variant low-pass filter. The filter can be applied in either the reprojection (i.e., forward projection) step or in the image domain on the estimated image prior to the reprojection. This process is much less computationally intensive than implementing micro-rays and micro-views as well as distance driven methods.

In an isocenter embodiment, the filter becomes spatially invariant and thus, has very fast processing. The system optics model accounts for the blur in the CT imaging chain. In this embodiment, the blur is measured, rather than modeled, using a calibration phantom consisting of a very small (1 mm or less in diameter), high-density, high-Z sphere suspended in a very low-density foam or other low-density supporting device and placed near the isocenter. This isocenter restriction is necessary because the blur depends on the location within the field-of-view.

Note that the cause of the blur, beam width, cross-talk, etc. is not important since it is being measured. Further, the isocenter approximation implies that one should get the benefit of the SOM for the image region near the isocenter and a reasonable approximation away from isocenter. The isocenter is often the most diagnostically important region of the image.

After the point spread function (PSF) is extracted from the measurements, which need only be done once at the factory, the PSF is used as a convolution kernel disposed after the forward projector in the IR loop. Note that the convolution operation is relatively inexpensive computationally compared with the other processing steps.

Certain variations upon the isocenter embodiment described above are given. In one embodiment, the measurement and use of the PSF is combined with distance-driven backprojection to incorporate backprojection blur caused by image voxel size on the detector cells. The PSF can be from a single measurement or better, averaged from multiple measurements around the isocenter so that the measurements are not biased due to a particular position, where the test sphere projects onto a "special" area of a detector cell. Note also that, instead of measurement, the PSF can be estimated using the micro-ray approach. However, this estimator does not include blurring sources such as cross-talk. In addition, the convolution of the PSF is more efficient if applied after log operations.

Figure 2:
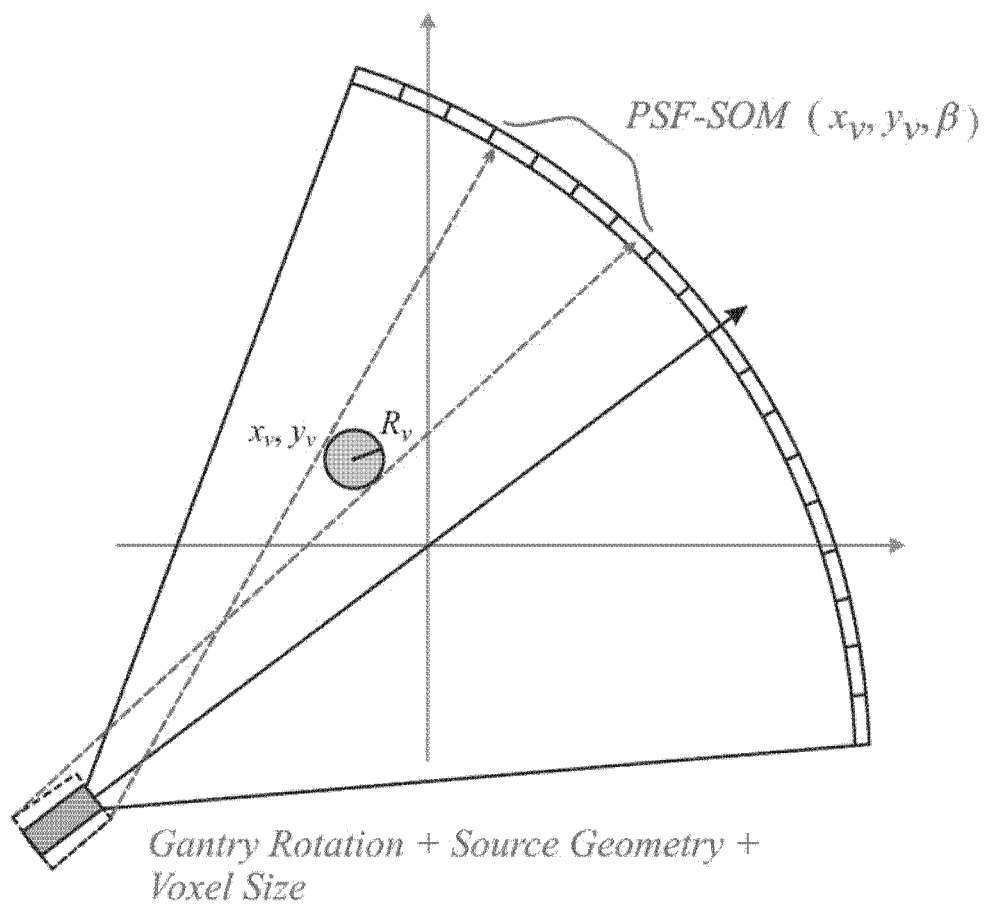
FIG. 2 is a graphical illustration of an X-ray beam emanating from an x-ray source according to one embodiment.

According to one embodiment, a data domain Iterative Reconstruction-System Optics Modeling (IR-SOM) Low-Pass Filter (DLPF) concept is disclosed. FIG. 2 illustrates the actual case of an X-ray beam emanating from an X-ray source through a material, and received at an array of X-ray detectors. For the given source geometry during gantry rotation, the projection of a voxel located at $x_v$, $y_v$ with radius $R_v$ on the X-ray detectors at a view angle, $\beta$, is given by PSF-SOM ($x_v$, $y_v$, $\beta$). A PSF describes the response of an imaging system to a point source or a point object. The PSF can be thought of as a system's impulse response for a focused optical system. As illustrated in FIG. 2, the right-front corner and the left-rear corner of the X-ray source cause a distortion or blurring, which is represented by the function PSF-SOM ($x_v$, $y_v$, $\beta$). Note, however, that not just the right-front corner and left-rear corner causes the blurring. The black dashed lines represent the area that the source traverses during acquisition of one view. All rays emanating from within the black dashed lines that intersect the material contribute to the blurring. The red dashed lines represent the boundary rays that define the boundary of the PSF. To keep the illustration simpler, the rays in between have not been drawn.

Figure 3:
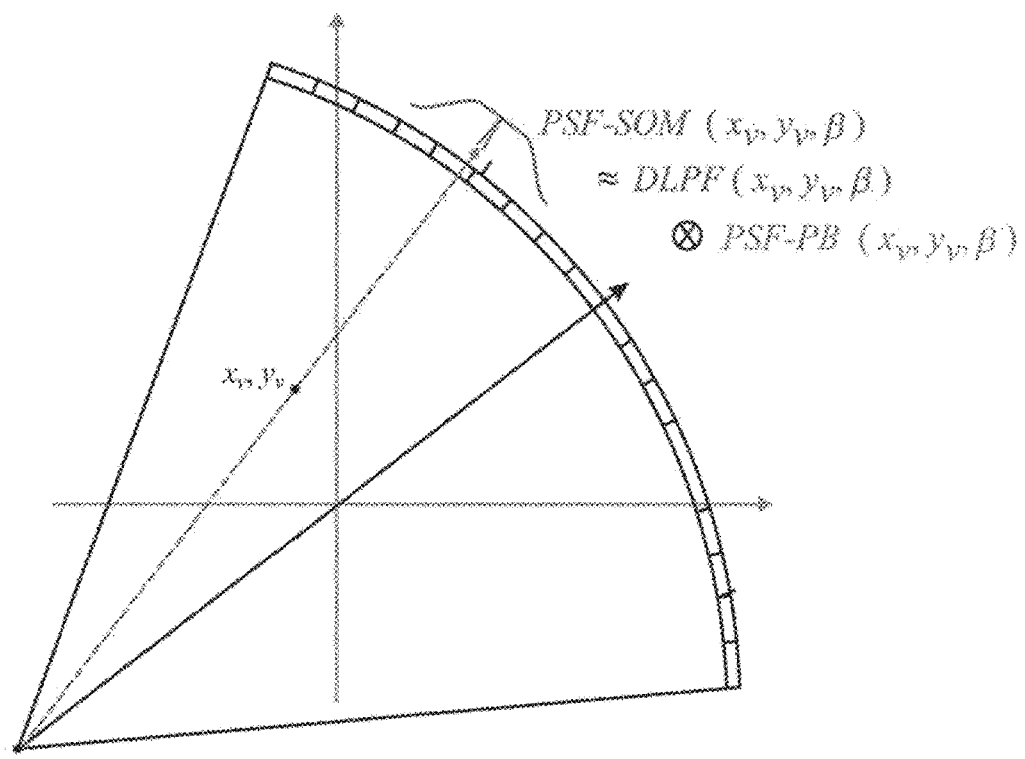
FIG. 3 is a graphical illustration of the example shown in FIG. 2, with a SOM applied using a data domain low-pass filter (DLPF) according to one embodiment.

FIG. 3 illustrates the same case from FIG. 2, but with a SOM applied using a data domain LPF (DLPF). In a DLPF-modelled case, a pencil beam (PB) geometry is assumed in IR, using a point source, a point voxel, and no gantry rotation blur. The projection of a point voxel is given by PSF-PB ($x_v$, $y_v$, $\beta$). Thus, the actual case of PSF-SOM ($x_v$, $y_v$, $\beta$) illustrated in FIG. 2 can be estimated by convolving PSF-PB ($x_v$, $y_v$, $\beta$) with the digital filter DLPF ($x_v$, $y_v$, $\beta$).

Figure 4:
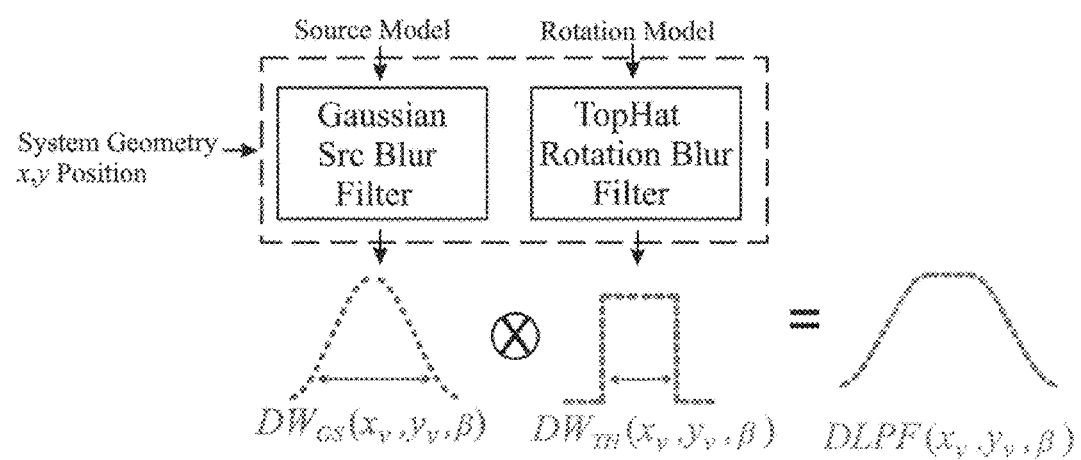
FIG. 4 illustrates a convolved curve that results for a data domain low-pass filter (DLPF $(x_v, y_v, \beta)$) according to one embodiment.

Further, the DLPF can be modeled as a convolution of two filters, a Gaussian filter and a TopHat filter, as shown in FIG. 4. The Gaussian filter is used to model the source and voxel blur, and the TopHat filter is used to model the rotation blur. The rotation blur is the result of gantry motion during data acquisition integration time. The full-width tenth max width of the Gaussian filter is given by $DW_{GS}$, and the full-width tenth max width of the TopHat filter is given by $DW_{TH}$. The two functions are convolved to produce the filter DLPF. FIG. 4 illustrates the convolved curve that results for DLPF ($x_v$, $y_v$, $\beta$).

Figure 5:
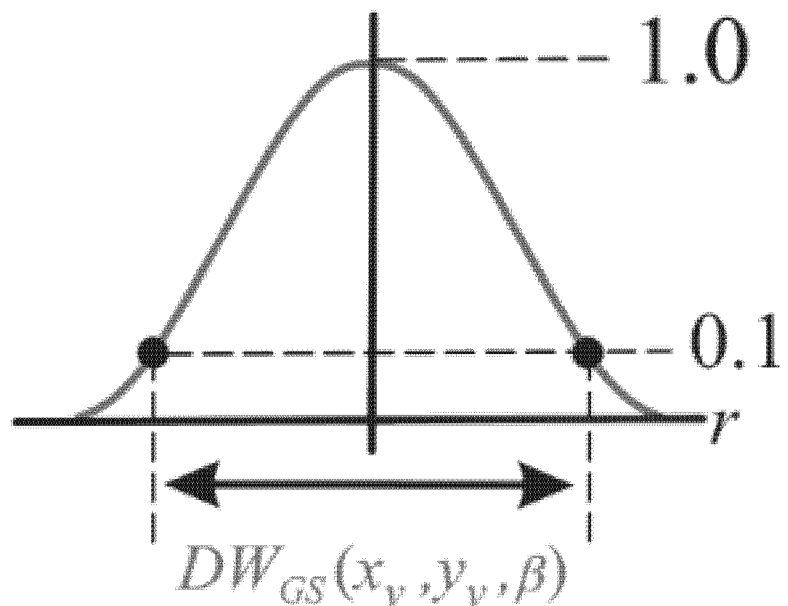
FIG. 5 is a graphical illustration of a Gaussian filter component according to one embodiment.

The shape of the Gaussian filter component is illustrated by the curve shown in FIG. 5. The full-width tenth max (FWTM) of the curve is given by $DW_{GS}$ ($x_v$, $y_v$, $\beta$). As a result, $$\sigma = \frac{DW_{GS}(x_v, y_v, \beta)}{2\sqrt{-2\ln P}}$$

wherein P=0.1 (full-width tenth max).

The discrete Gaussian filter (DGS) is given by:

$$DGS_{xv,yv,\beta}[i] = e^{\frac{-(s+i \cdot \Delta c)^2}{2\sigma^2}} \quad s = -\frac{NPts_{GS} \cdot \Delta c}{2} \quad 0 \leq i < NPts_{GS}$$

where $\Delta c$=Channel spacing in channels, nominally 1.0, which results in:

$$DGS_{xv,yv,\beta}(r) = 1.0 e^{\frac{-r^2}{2\sigma^2}}$$

with a number of points, $$NPts_{GS\ xv,yv,\beta} = \text{int}\left\{1.5 \cdot \left(1.0 + \frac{DW_{GS}(x_v, y_v, \beta)}{\Delta c}\right)\right\} \text{ if}$$

$NPts_{GS}$ even, $NPts_{GS}$ ++

Figure 6:
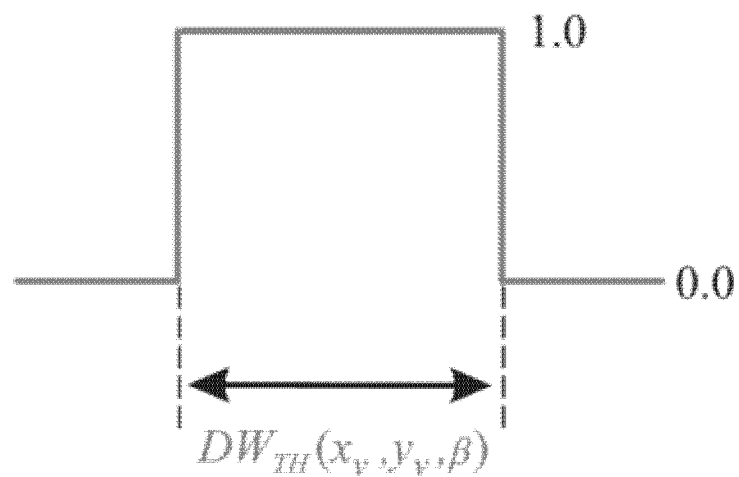
FIG. 6 is a graphical illustration of a TopHat filter component according to one embodiment.

The shape of the TopHat filter component is illustrated by the curve shown in FIG. 6, where:

$$DTH_{xv,yv,\beta}(r) = 1.0 \text{ for}$$

$$\left\{-\frac{DW_{TH}(x_v, y_v, \beta)}{2} \leq r \leq \frac{DW_{TH}(x_v, y_v, \beta)}{2}\right\}$$

0.0 otherwise.

The discrete TopHat filter (DTH) is given by:

$$DTH_{xv,yv,\beta}[i] = 1.0 \quad 0 \leq i < NPts_{TH}$$

with a number of points, $$NPts_{TH\ xv,yv,\beta} = \text{int}\left\{\frac{DW_{TH}(x_v, y_v, \beta)}{\Delta c}\right\} \text{ if}$$

$NPts_{TH}$ even, $NPts_{TH}$ ++

FIG. 7 illustrates a final DLPF filter, which is the discrete convolution of the discrete TopHat filter, DTH, and the discrete Gaussian filter, DGS. The filter is normalized after convolution, using the following normalizing equation:

$$DLPF_{xv,yv,\beta}[i] = \frac{1}{A_o} \cdot DLPF'_{xv,yv,\beta}[i]$$

$$A_o = \sum_{i=0}^{NPts_{DLPF}-1} DLPF'[i]$$

where DLPF' is the un-normalized filter directly after convolution.

Figure 8:
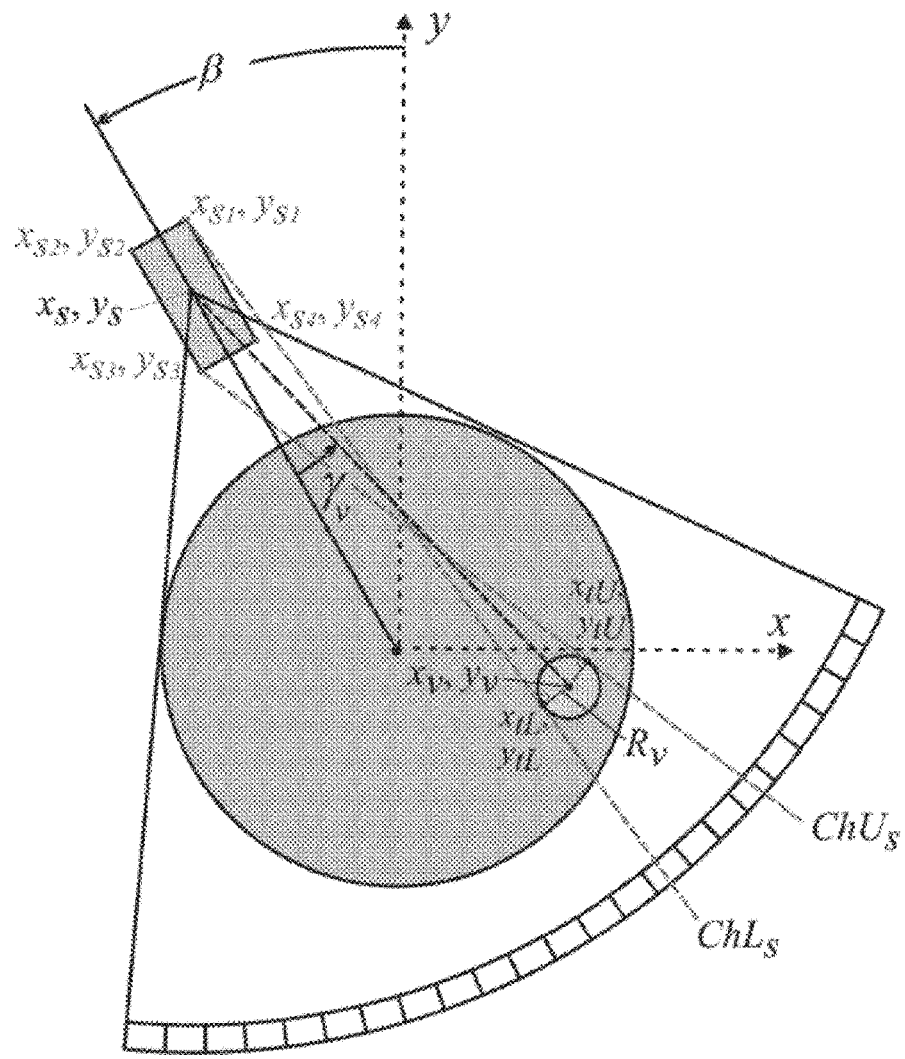
FIG. 8 is a graphical illustration of a Gaussian width according to one embodiment.

A calculation of the Gaussian width, $DW_{GS}$ will be given with reference to FIG. 8. Here, $$DW_{GS}(x_v, y_v, \beta) = ChFP_{SOM}(x_v, y_v, \beta) \cdot GSScale$$

wherein $ChFP_{SOM}(x_v, y_v, \beta)$ is the footprint of the voxel at $(x_v, y_v, \beta)$ due to the SOM source, and GSScale is an empirically determined parameter (e.g., 0.67). The SOM source footprint is given by:

$$ChFP_{SOM}(x_v, y_v, \beta) = ChU - ChL$$

A rectangular source in the x-y plane is defined by center point $(x_s, y_s)$ and corner points $(x_{s1}, y_{s1})$ through $(x_{s4}, y_{s4})$. For each corner point $(x_{sn}, y_{sn})$, a ray emanating from the source point will be tangent to the voxel at $(x_v, y_v)$ at points $(x_t, y_t)$ and will intersect the detector at channel Ch. The SOM source footprint is the maximum and minimum channel positions determined from all four source corner points. For $\gamma_v \geq 0$, ChL is defined by ray S1tL, and ChU by rays from S3tU. For $\gamma_v < 0$, ChL is defined by ray S4tL and ChU by ray S2tU.

A calculation of the TopHat width, $DW_{TH}$ will be given with reference to FIG. 9. In particular:

$$DW_{TH}(x_v, y_v, \beta) = ChFP_{ROT}(x_v, y_v, \beta) \cdot THScale$$

wherein $ChFP_{ROT}(x_v, y_v, \beta)$ is the footprint of the voxel at $(x_v, y_v, \beta)$ due to the rotation of a point source during the integration time, and THScale is an empirically determined parameter (e.g., 0.9). The rotation footprint is given by:

$$ChFP_{ROT}(x_v, y_v, \beta) = \max(ChU_{vs}, ChU_{ve}) - \min(ChL_{vs}, ChL_{ve})$$

Figure 9:
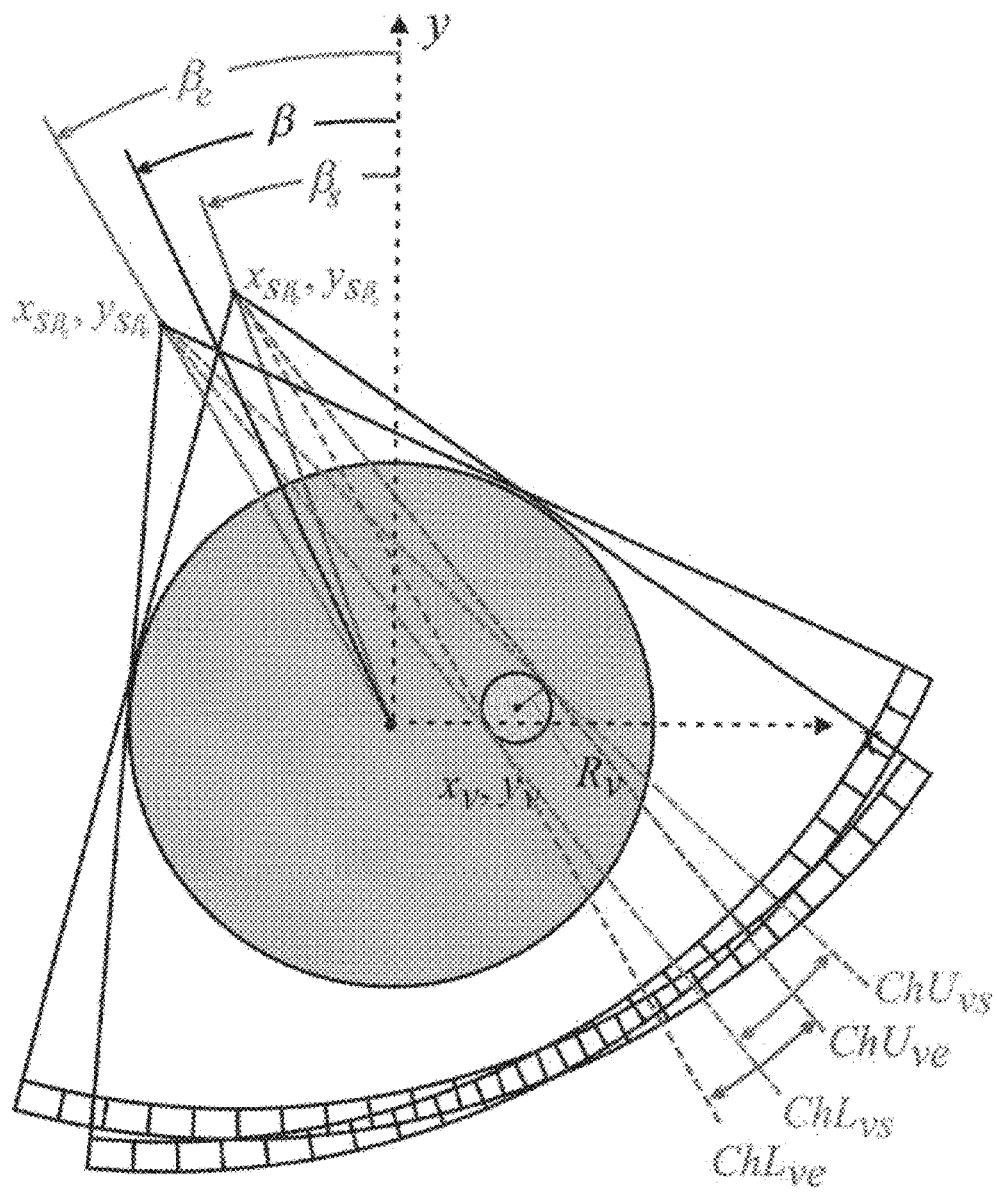
FIG. 9 is a graphical illustration of a TopHat width according to one embodiment.

In FIG. 9, the voxel footprint for the source at starting view $\beta_s$ is defined by $ChL_{vs}$ and $ChU_{vs}$, and by $ChL_{ve}$ and $ChU_{ve}$ for view $\beta_e$. The rotation blur footprint is defined by the starting and ending view angles $\beta_s$ and $\beta_e$, corresponding to the start and end of DAS integration time for view $\beta_s$. Similar for $ChFP_{SOM}$, rays emanating from the source point tangent to the voxel will intersect the detector at channel Ch. For $ChFP_{ROT}$, the rays and channel intersections are calculated for the single source point at the starting and ending view positions.

Figure 10:
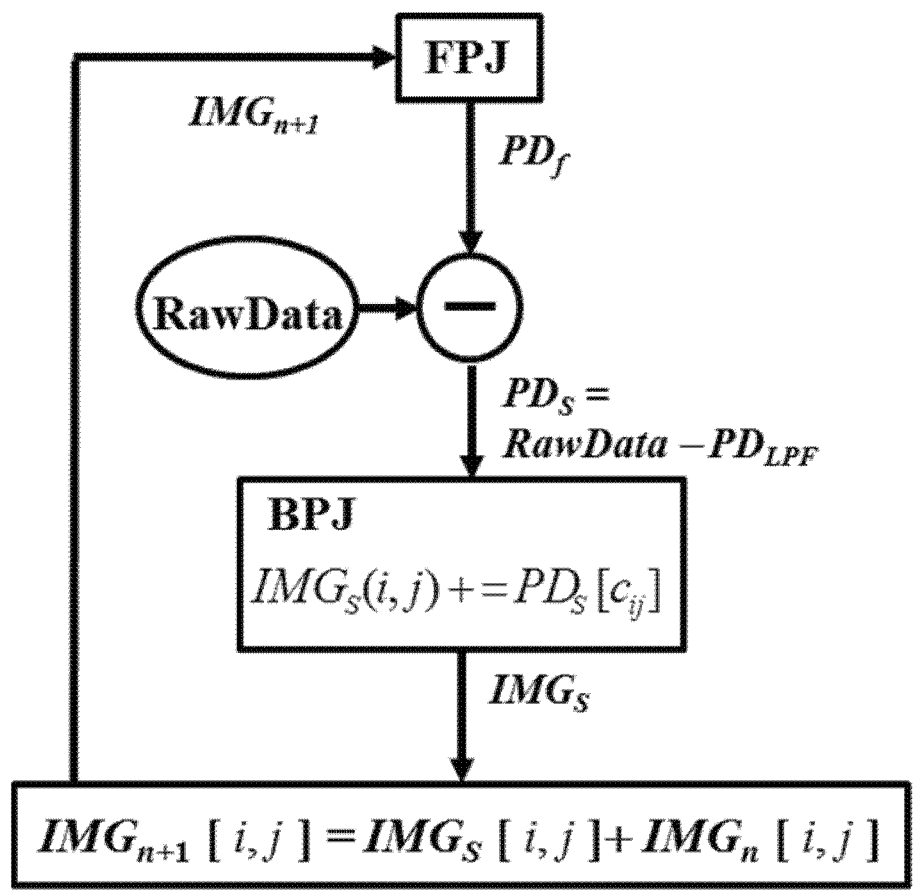
FIG. 10 is a flowchart which illustrates an IR flow according to one embodiment.

FIG. 10 is a flowchart which illustrates a typical IR flow. The current forward-projected data PDf is subtracted from the original RawData, which is backprojected to create current image $IMG_S$. $IMG_S$ is added to the previous image $IMG_n$ to create the updated image, $IMG_{n+1}$.

Figure 11:
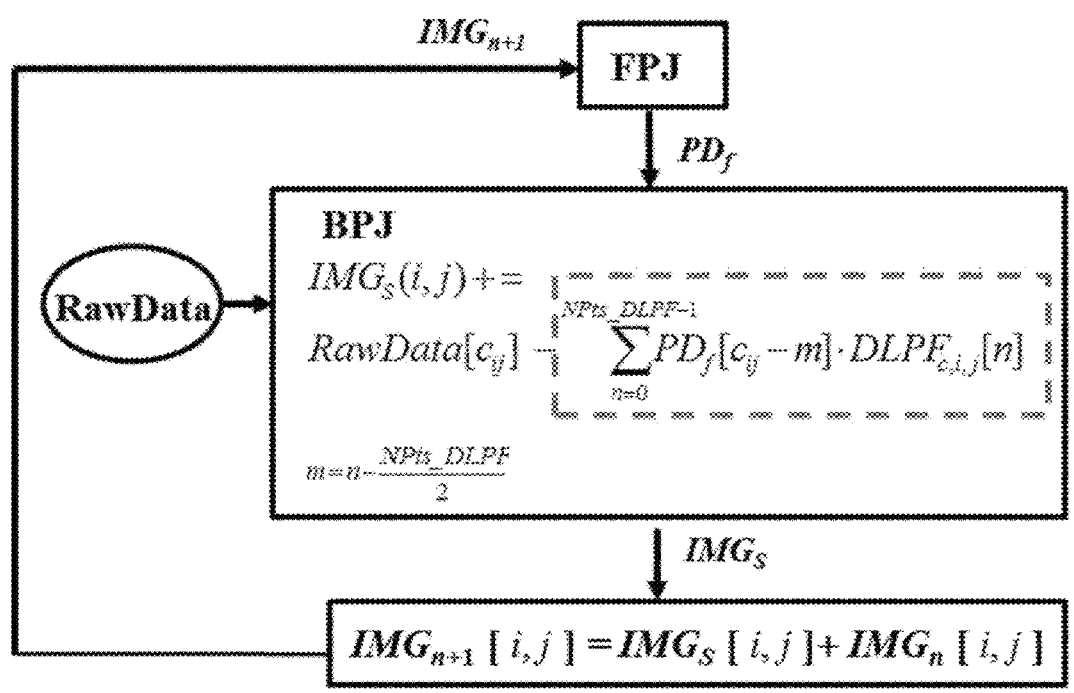
FIG. 11 is a flowchart which illustrates implementation of DLPF into the IR flow according to one embodiment.

FIG. 11 is a flowchart which illustrates implementation of DLPF into the IR flow. Since the filter is spatially dependent and must be applied to PDf and not PDs, the filter must be applied during backprojection, as illustrated by the dashed box in the equation below.

$$IMG_S(i, j) \mathrel{+}=$$

$$RawData[c_{ij}] - \boxed{\sum_{n=0}^{NPts\_DLPF-1} PD_f[c_{ij} - m] \cdot DLPF_{c,i,j}[n]}$$

$$m = n - \frac{NPts\_DLPF}{2}$$

FIG. 11 illustrates that the current image $IMG_S[i,j]$ is combined with a previously-obtained image $IMG_n[i,j]$, which results in an updated image $IMG_{n+1}[i,j]$.

Figure 12:
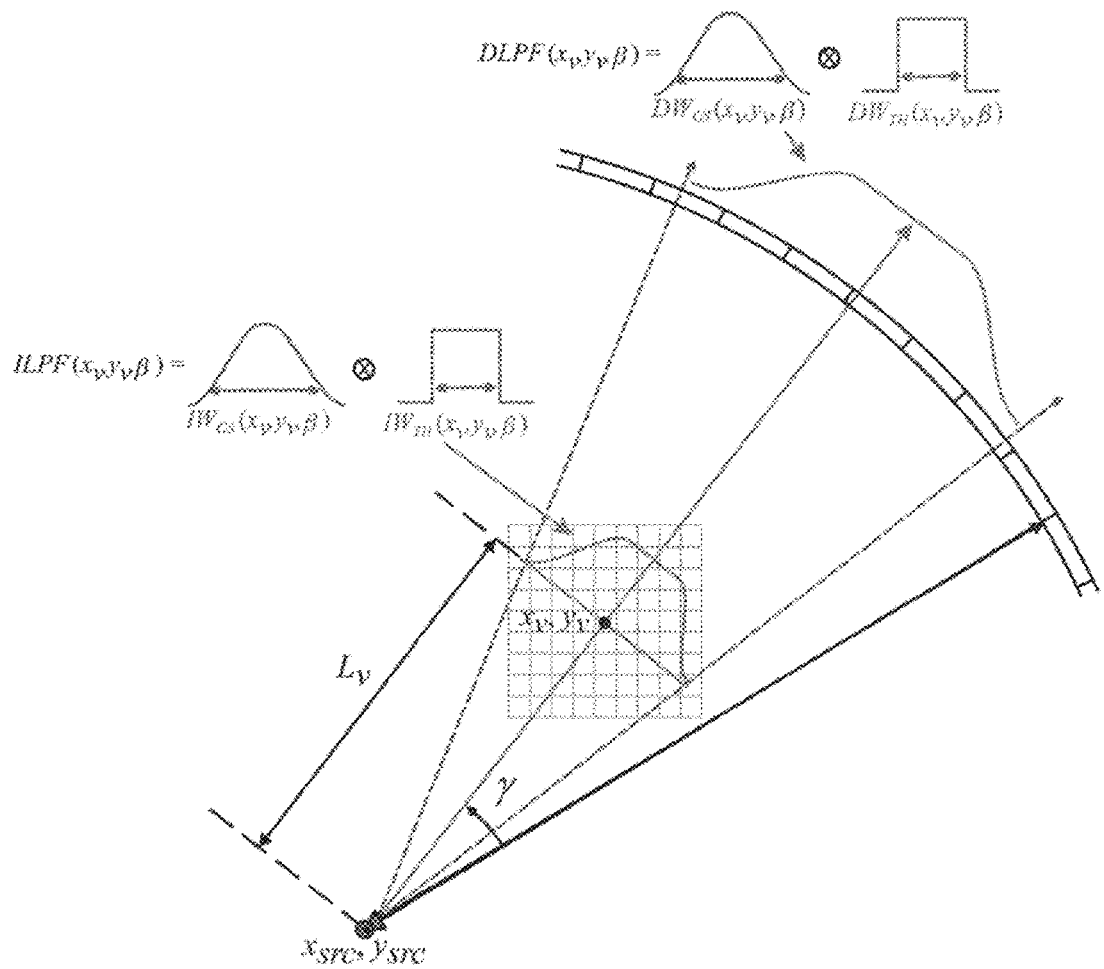
FIG. 12 is a graphical illustration of an image domain IR-SOM LPF according to one embodiment.

FIG. 12 illustrates an embodiment of an image domain IR-SOM LPF. Data domain filters can be converted to image domain filters and applied to image data, rather than projection data. The image domain equivalents of $DW_{TH}$ and $DW_{GS}$ are $IW_{TH}$ and $IW_{GS}$, respectively. Data-domain-to-image-domain filter lengths are represented as:

$$IW_{GS}(x_v, y_v, \beta) = 2 \cdot L_v \tan\left\{\frac{\Delta\gamma \cdot DW_{GS}(x_v, y_v, \beta)}{2}\right\}$$

$$IW_{TH}(x_v, y_v, \beta) = 2 \cdot L_v \tan\left\{\frac{\Delta\gamma \cdot DW_{TH}(x_v, y_v, \beta)}{2}\right\}$$

where $$L_v = \sqrt{(x_{src} - x_v)^2 + (y_{src} - y_v)^2}$$

$$\Delta\gamma = \frac{FanAngle}{NCh}$$

The image domain filter ILPF is calculated in the same manner as the DLPF described above, the only difference being $DW_{TH}$, $DW_{GS}$, $D_{TH}$, $D_{GS}$, DLPF, and $NPts_{DLPF}$ are replaced with their image-domain counterparts, $IW_{TH}$, $IW_{GS}$, ITH, IGS, ILPF, and $NPts_{ILPF}$. $\Delta c$ has also been replaced with $\Delta xy$, where $\Delta xy$ is the voxel spacing in mm.

Figure 13:
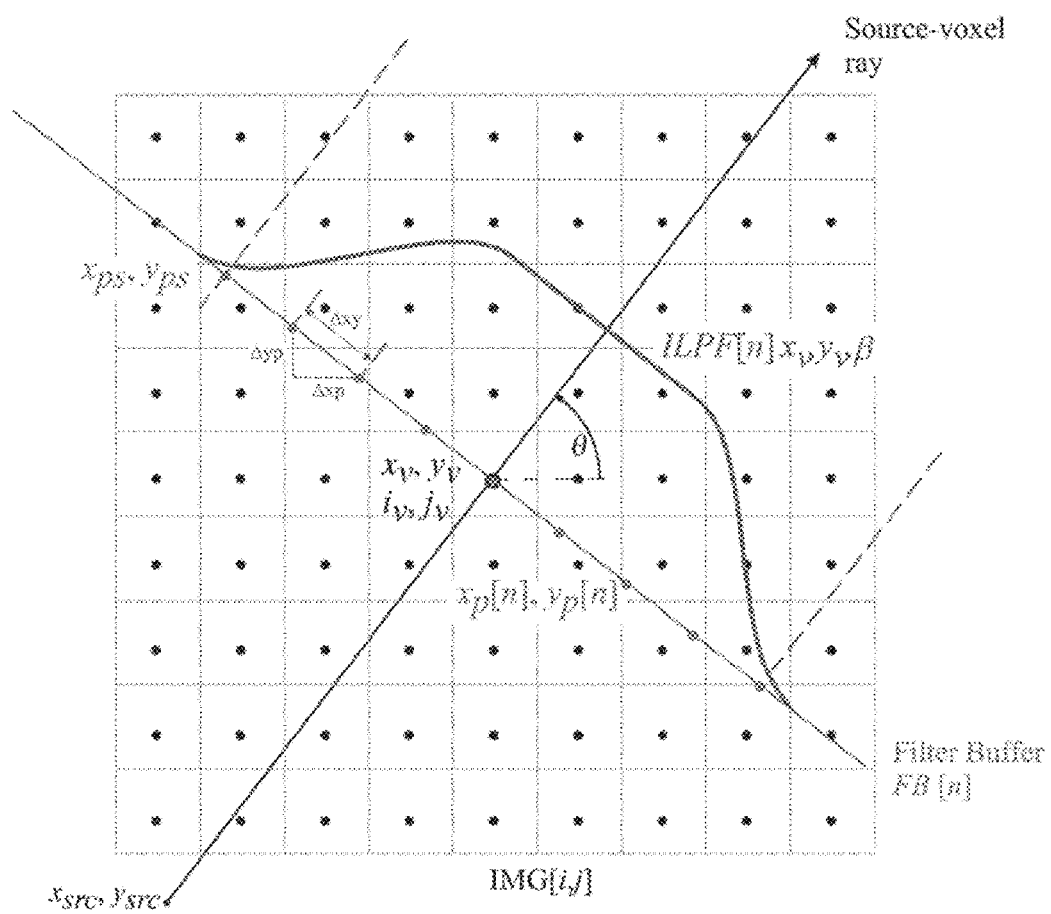
FIG. 13 is a graphical illustration of an implementation of an image domain IR-SOM LPF according to one embodiment.

FIG. 13 illustrates an implementation of an image domain, IR-SOM LPF. Image voxels are 1-D and are filtered along a 1-D line, which is perpendicular to the source-voxel ray passing through the voxel to be filtered, $x_v, y_v$. Voxel values at $x_p, y_p$ along the filtering line are calculated from IMG by bilinear interpolation (BLI) or nearest neighbor into a filter buffer, FB. The FB is filtered to generate the output voxel $IMGF[i_v, j_v]$, as given below.

$$IMGF[i_v, j_v] = \sum_{n=0}^{NPts_{ILPF}-1} FB[n] \cdot ILPF[n]_{x_v, y_v, \beta}$$

where $$FB[n] = BLI\{IMG(i_{xp[n]}, j_{xp[n]})\}$$

$$i_{xp}[n] = \frac{x_p[n] - x_o}{\Delta xy} \quad j_{yp}[n] = \frac{y_p[n] - y_o}{\Delta xy}$$

$$x_p[n] = x_{ps} + n \cdot \Delta x_p \quad y_p[n] = y_{ps} + n \cdot \Delta y_p$$

$$\Delta x_p = \Delta xy \cdot \sin(\theta) \quad \Delta y_p = -\Delta xy \cdot \cos(\theta)$$

$$x_{ps} = -\frac{NPts_{ILPF}}{2} \cdot \Delta xy \cdot \sin\theta + x_v$$

$$y_{ps} = \frac{NPts_{ILPF}}{2} \cdot \Delta xy \cdot \cos\theta + y_v$$

$$m = \frac{y_v - y_{src}}{x_v - x_{src}} \quad \theta = \tan^{-1} m$$

Figure 14:
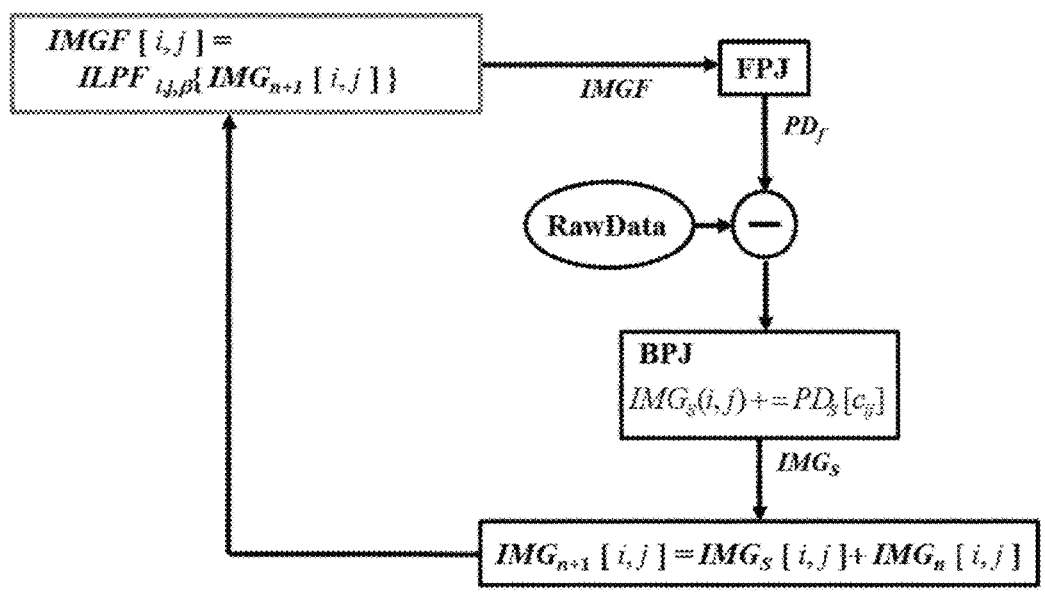
FIG. 14 is a flowchart, which illustrates an image domain flow IR-SOM LPF according to one embodiment.

FIG. 14 is a flowchart that illustrates an image domain flow IR-SOM LPF. Image domain filtering is usually applied to the image prior to forward projection, and therefore forward projection (FPJ) and back projection (BPJ) do not have to be modified.

Figure 15:
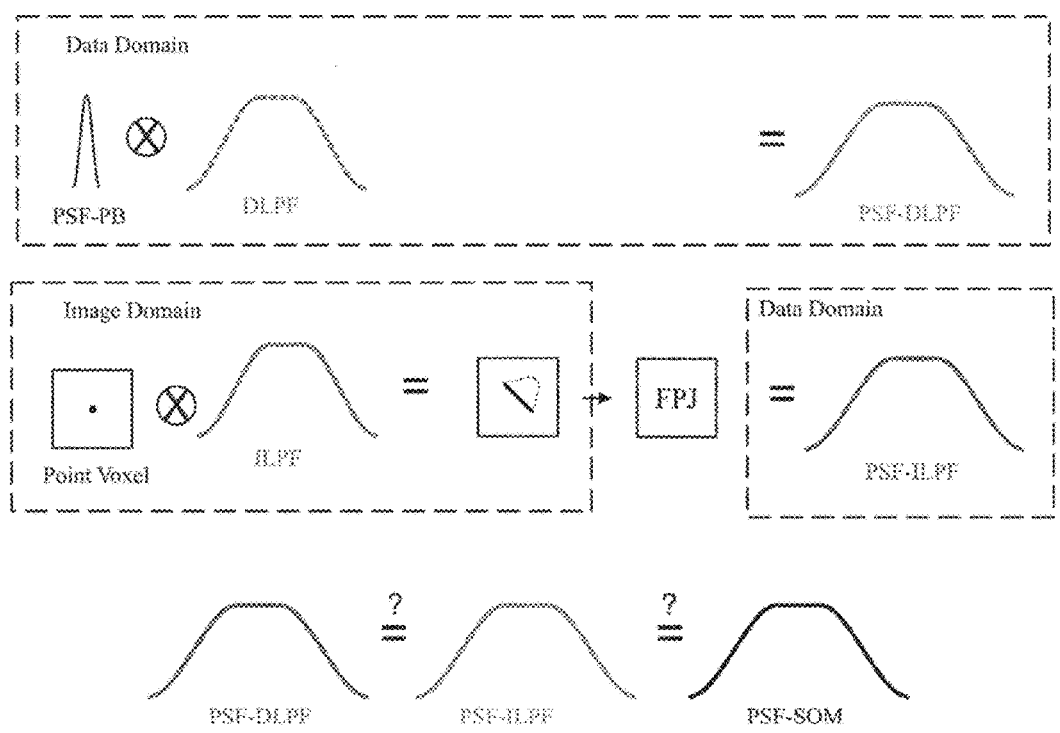
FIG. 15 illustrates a verification of the data domain and the image domain being equivalent according to one embodiment.

A verification scheme to show that the data domain and the image domain implementations are equivalent will be given with reference to FIG. 15. A pencil-beam point-spread function (PB-PSF) convolved with DLPF should match the system object model point-spread function (SOM-PSF), as illustrated in the first box of FIG. 15. In addition, a forward-projected point voxel convolved with ILPF should match the SOM-PSF, as illustrated in the second box of FIG. 15.

Figure 16:
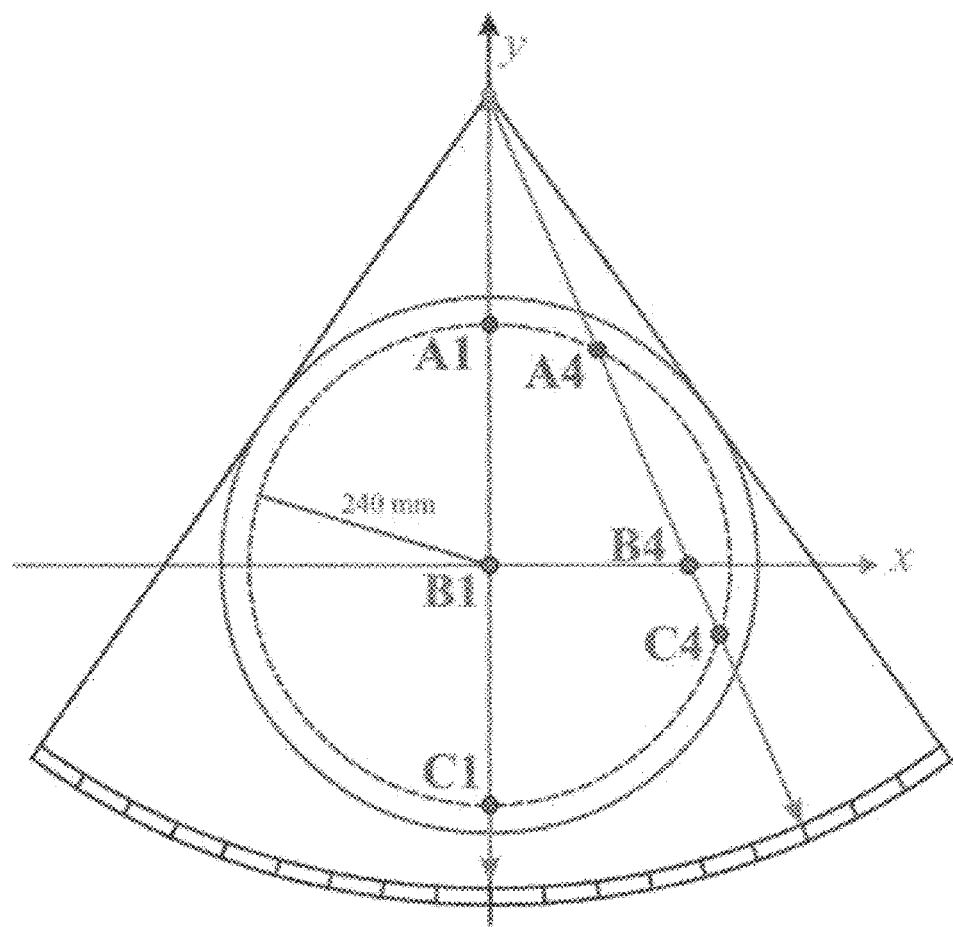
FIG. 16 is a simulated point spread function (PSF) phantom used to generate of projection data for validation according to one embodiment.
Figure 17A:
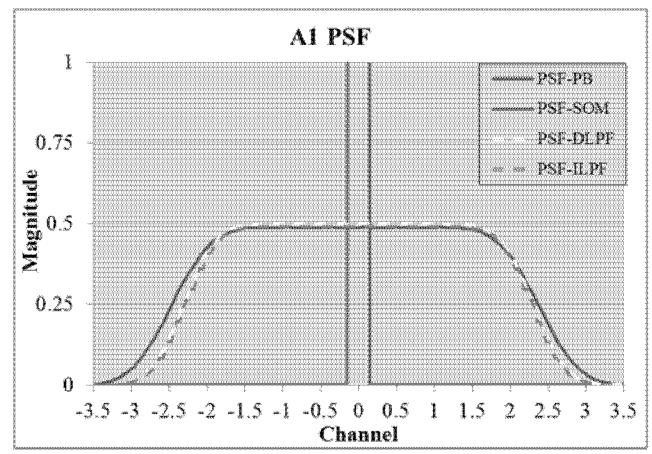
FIGS. 17A-17F are graphical illustrations that compare the data domain, image domain, and true PSFs for the phantom in FIG. 16 according to one embodiment.
Figure 17B:
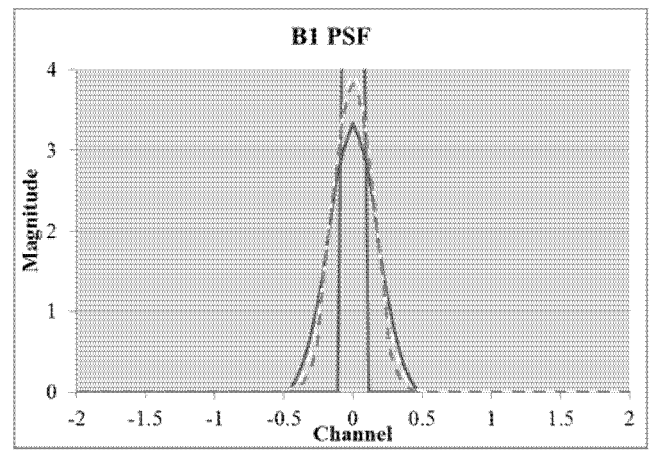
Figure 17C:
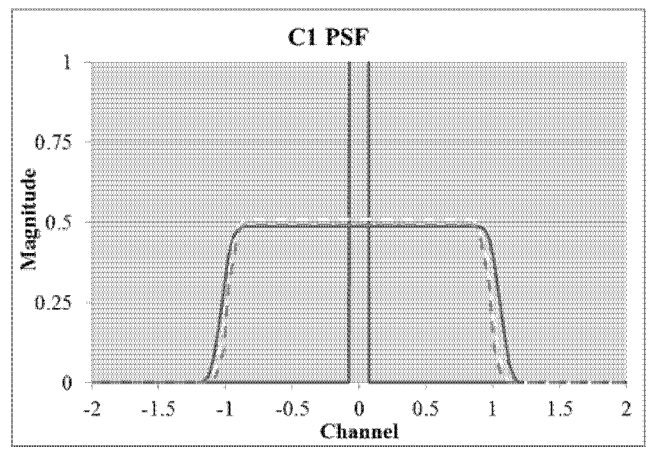
Figure 17D:
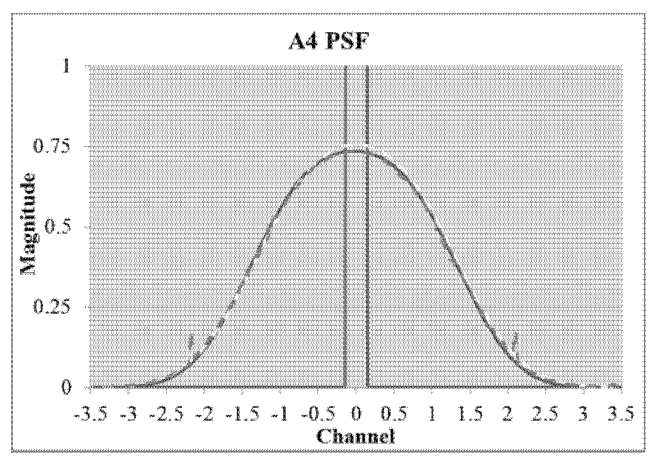
Figure 17E:
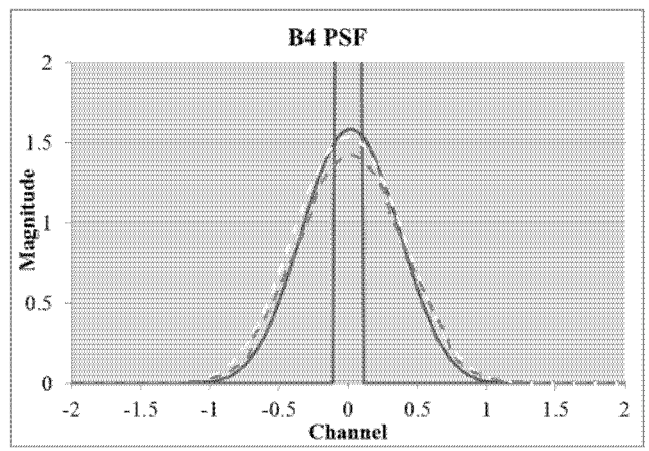
Figure 17F:
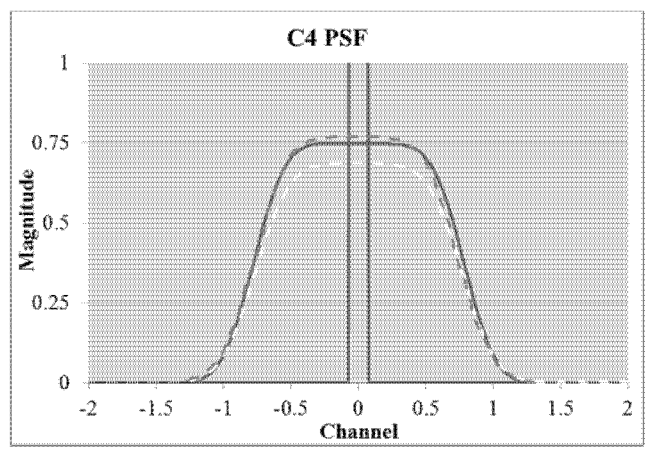

Simulated PSF projection data for a thin wire located at various x, y positions is generated for PSF-SOM conditions, as well as PSF-PB conditions, as illustrated in FIG. 16. A simulated point voxel image is also generated.

FIGS. 17A-17F compare the data domain implementation to the image domain implementation for a PSF for the six different points illustrated in FIG. 16. The plots compare an actual real case with a system optical modeling (PSF-SOM), a pencil-beam case (PSF-PB), a data-domain low-pass filter convolved with PSF-PB (PSF-DLPF), and an image-domain low-pass filter (PSF-ILPF). As illustrated for each of the six points, the data domain PSF-DLPF and the image domain PSF-ILPF are very similar to each other and the actual case PSF-SOM.

FIG. 18 is a flowchart for a method 1800 of reconstructing a detected X-ray from an X-ray source of a computed tomography (CT) scanner. The method includes obtaining projection data, via a processing circuit, collected by a CT detector during a scan of an object in step S1810.

The method also includes performing iterative reconstruction of the projection data by filtering forward projected data during backprojection to model system optics in step S1820.

The method also includes subtracting the filtered forward projected data from the projection data to generate a current image in step S1830.

The method also includes combining the current image with a previously-obtained image to generate an updated image in step S1840.

The method 1800 can also include projecting a voxel at a given location onto one or more X-ray detectors at a given view angle, and obtaining a PSF for the projected voxel. The method 1800 can also include convolving a projected point voxel with a data-domain low-pass filter for the given location. The data-domain low-pass filter can be modeled as a full-width tenth max width of the Gaussian blur function convolved with a full-width tenth max width of the TopHat blur function.

A computer-readable medium having computer-executable instructions embodied thereon, can cause a computing device to perform the above-described method.

In the disclosed embodiments, a CT scanning apparatus, such as the apparatus described above with reference to FIG. 1, includes processing circuitry for combining imaging iterative reconstruction with a system optics model (SOM). The SOM can have a spatially variant filter in the data domain. The spatially variant filter in the data domain can have measurements of a calibration pin phantom at or near an isocenter of a field-of-view. The spatially variant filter in the data domain can also include a position-dependent Gaussian function representing a blur of the X-ray source, an associated X-ray detector, or voxel contributions. The spatially variant filter in the data domain can be convolved with a position dependent TopHat function representing a gantry rotation blur during a data sample. The convolved spatially variant filter can further be convolved with forward projected data of the imaging iterative reconstruction calculation. The SOM can also have a spatially variant filter in an image domain. The spatially variant filter in the image domain can contain a spatial dependent convolution of a Gaussian function and a TopHat function.

Embodiments of the IR approach described herein have better low-dose image quality compared to filtered backprojection. Embodiments described herein also have better edge and feature preservation and in some cases, improved spatial resolution, compared to standard IR. Embodiments described herein incorporate non-linear, spatial variant de-convolution into iterative reconstruction-based algorithms, which are much more computational efficient than conventional methods.

The above-described embodiments can be implemented, in part, using a memory, a processor, and circuitry of a computing system, such as the computing system illustrated in FIG. 19. In FIG. 19, the computing system includes a CPU 1900 which performs the processes described above. The process data and instructions may be stored in memory 1902. These processes and instructions may also be stored on a storage medium disk 1904 such as a hard drive (HDD) or portable storage medium or may be stored remotely. Further, the claimed embodiments are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing system communicates, such as a server or computer.

Further, the claimed embodiments may be provided as a utility application, background daemon, or component of an operating system, or combination thereof, executing in conjunction with CPU 1900 and an operating system such as Microsoft Windows 7, UNIX, Solaris, LINUX, Apple MAC-OS and other systems known to those skilled in the art.

CPU 1900 may be a Xenon or Core processor from Intel of America or an Opteron processor from AMD of America, or may be other processor types that would be recognized by one of ordinary skill in the art. Alternatively, the CPU 1900 may be implemented on an FPGA, ASIC, PLD or using discrete logic circuits, as one of ordinary skill in the art would recognize. Further, CPU 1900 may be implemented as multiple processors cooperatively working in parallel to perform the instructions of the inventive processes described above.

The computing system in FIG. 19 also includes a network controller 1906, such as an Intel Ethernet PRO network interface card from Intel Corporation of America, for interfacing with network 19. As can be appreciated, the network 19 can be a public network, such as the Internet, or a private network such as an LAN or WAN network, or any combination thereof and can also include PSTN or ISDN sub-networks. The network 19 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing system further includes a display controller 1908, such as a NVIDIA GeForce GTX or Quadro graphics adaptor from NVIDIA Corporation of America for interfacing with display 1910, such as a Hewlett Packard HPL2445w LCD monitor. A general purpose I/O interface 1912 interfaces with a keyboard and/or mouse 1914 as well as a touch screen panel 1916 on or separate from display 1910. General purpose I/O interface 1912 also connects to a variety of peripherals 1918 including printers and scanners, such as an OfficeJet or DeskJet from Hewlett Packard.

A sound controller 1920 is also provided in the computing system, such as Sound Blaster X-Fi Titanium from Creative, to interface with speakers/microphone 1922 thereby providing sounds and/or music.

The general purpose storage controller 1924 connects the storage medium disk 1904 with communication bus 1926, which may be an ISA, EISA, VESA, PCI, or similar, for interconnecting all of the components of the computing system. A description of the general features and functionality of the display 1910, keyboard and/or mouse 1914, as well as the display controller 1908, storage controller 1924, network controller 1906, sound controller 1920, and general purpose I/O interface 1912 is omitted herein for brevity as these features are known.

While certain embodiments have been described, these embodiments have been presented by way of example only, and are not intended to limit the scope of the disclosures. The novel methods and systems described herein may be embodied in a variety of other forms. Furthermore, various omissions, substitutions, and changes in the form of the methods and systems described herein may be made without departing from the spirit of the disclosures. The accompanying claims and their equivalents are intended to cover such forms or modifications as would fall within the scope and spirit of the disclosures.

The invention claimed is:

1. A computed tomography (CT) imaging apparatus, comprising:
    a processing circuit configured to
        obtain projection data collected by a CT detector during a scan of an object;
        perform iterative reconstruction of the projection data to generate a current image, each cycle of the iterative reconstruction including filtering the current image before forward projection with a filter that models system optics and operates on image data; and
    combine the current image with a previously-obtained image to generate an updated image.

2. The CT imaging apparatus of claim 1, wherein the processing circuit is further configured to perform the filtering using a low-pass filter in an image domain.

3. The CT imaging apparatus of claim 1, wherein the processing circuit is further configured to perform the filtering using a spatially variant filter in an image domain.

4. The CT imaging apparatus of claim 3, wherein the spatially variant filter includes a position-dependent Gaussian blur function that represents one or more of an X-ray source, an associated detected X-ray, and voxel contributions.

5. The CT imaging apparatus of claim 4, wherein the processing circuit is further configured to perform the filtering using the spatially variant filter convolved with a position-dependent TopHat function that represents a gantry rotation blur.

6. The CT imaging apparatus of claim 1, wherein in generating the current image, the processing circuit is further configured to subtract forward-projected data from the projection data.

7. The CT imaging apparatus of claim 1, wherein the processing circuit is further configured to perform the filtering using a spatially variant filter, which is obtained by convolving a Gaussian function and a TopHat function.

8. The CT imaging apparatus of claim 1, further comprising:
    an X-ray source to emit X-rays during the scan of the object; and
    the CT detector to collect the projection data.

9. A method of performing image reconstruction, comprising:
    obtaining projection data collected by a computed tomography detector during a scan of an object;
    performing iterative reconstruction (IR) of the projection data to generate a current image, each cycle of the iterative reconstruction including filtering the current image before forward projection with a filter that models system optics and operates on image data; and
    combining the current image with a previously-obtained image to generate an updated image.

10. The method of claim 9, further comprising:
    subtracting current forward projected data from original projection data collected in a computer memory;
    backprojecting a result of the subtracting to create the current image; and
    adding the current image to a previously-obtained image.

11. The method of claim 10, wherein the filtering step comprises filtering using a spatially-variant filter in a one-dimensional convolution with an image perpendicular to a ray-sum path, after each forward projection step of the IR.

12. The method of claim 11, wherein the spatially-variant filter is in an image domain.

13. The method of claim 12, wherein the spatially-variant filter has a position-dependent Gaussian blur function that represents one or more of the X-ray source, the detected X-ray, and voxel contributions.

14. The method of claim 11, further comprising convolving the spatially-variant filter with a position-dependent TopHat blur function representing a gantry rotation during a data sample.

15. The method of claim 9, further comprising:
    projecting a voxel at a given location onto one or more X-ray detectors at a given view angle; and
    obtaining a point spread function for the projected voxel.

16. The method of claim 15, further comprising:
    convolving a projected point voxel with a data domain low-pass filter for the given location.

17. The method of claim 16, wherein the data domain low-pass filter is modeled as a full-width tenth max width of the Gaussian blur function convolved with a full-width tenth max width of the TopHat blur function.

18. The method of claim 9, further comprising:
    subtracting forward-projected data from the projection data.

19. A non-transitory computer-readable medium storing computer-executable instructions that, when executed by a processing circuit, cause the processing circuit to perform a method, comprising:
    obtaining projection data collected by a computed tomography detector during a scan of an object;
    performing iterative reconstruction of the projection data to generate a current image, each cycle of the iterative reconstruction including filtering the current image before forward projection with a filter that models system optics and operates on image data; and
    combining the current image with a previously-obtained image to generate an updated image.

20. The computer-readable medium of claim 19, wherein the filter is a spatially-variant filter in an image domain.

* * * * *